(12) United States Patent
Suh et al.

(10) Patent No.: US 9,782,765 B2
(45) Date of Patent: Oct. 10, 2017

(54) MESOPOROUS COMPOSITE OXIDE CATALYST, METHOD FOR PREPARING THE SAME AND METHOD FOR SYNTHESIZING 1,3-BUTADIENE USING THE SAME

(71) Applicant: LG Chem, Ltd., Seoul (KR)

(72) Inventors: Myung Ji Suh, Daejeon (KR); Dong Hyun Ko, Daejeon (KR); Kyong Yong Cha, Daejeon (KR); Jun Han Kang, Daejeon (KR); Dae Chul Kim, Daejeon (KR); Hyun Seok Nam, Daejeon (KR); Dae Heung Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 183 days.

(21) Appl. No.: 14/418,027

(22) PCT Filed: May 2, 2014

(86) PCT No.: PCT/KR2014/003950
§ 371 (c)(1),
(2) Date: Jan. 28, 2015

(87) PCT Pub. No.: WO2014/182018
PCT Pub. Date: Nov. 13, 2014

(65) Prior Publication Data
US 2015/0151292 A1  Jun. 4, 2015

(30) Foreign Application Priority Data

| May 6, 2013 | (KR) | ........................ 10-2013-0050408 |
| Apr. 30, 2014 | (KR) | ........................ 10-2014-0052496 |

(51) Int. Cl.
*C07C 5/48* (2006.01)
*B01J 21/08* (2006.01)
(Continued)

(52) U.S. Cl.
CPC .............. *B01J 37/031* (2013.01); *B01J 21/08* (2013.01); *B01J 23/002* (2013.01);
(Continued)

(58) Field of Classification Search
None
See application file for complete search history.

(56) References Cited

U.S. PATENT DOCUMENTS

| 5,132,269 A | 7/1992 | Sasaki et al. |
| 5,144,090 A * | 9/1992 | Honda .................. B01J 23/002 |
| | | 568/469.9 |

(Continued)

FOREIGN PATENT DOCUMENTS

| EP | 1930074 A1 | 6/2008 |
| EP | 2343123 A3 | 10/2011 |

(Continued)

OTHER PUBLICATIONS

Hengquan Yang, "Hoveyda-Grubbs catalyst confined in the nanocages of SBA-1: enhanced recyclability for olefin metathesis" Chem Commun. vol. 46, p. 8659-8661, 2010.
Hengquan Yang, et al., "Hoveyda-Grubbs catalyst confined in the nanocages of SBA-1: enhanced recyclability for olefin metathesis", The Royal Society of Chemistry 2010, Chem. Commun., 2010, vol. 46, pp. 8659-8661.

*Primary Examiner* — Philip Louie
(74) *Attorney, Agent, or Firm* — Dentons US LLP

(57) ABSTRACT

Disclosed are a mesoporous composite oxide catalyst, a method for preparing the same and a method for synthesizing 1,3-butadidne using the same. The surface area is increased by introducing certain porous silica into preparation of a catalyst for synthesizing 1,3-butadiene, thereby improving a conversion ratio of normal-butene, and selectivity and yield of 1,3-butadiene, and providing economic efficiency from the viewpoint of decreasing an amount of used metal and reducing catalyst production cost.

14 Claims, 5 Drawing Sheets

(51) Int. Cl.
*B01J 23/31* (2006.01)
*B01J 37/03* (2006.01)
*B01J 23/887* (2006.01)
*B01J 35/10* (2006.01)
*B01J 29/03* (2006.01)
*B01J 35/00* (2006.01)
*B01J 37/02* (2006.01)
*B01J 23/00* (2006.01)

(52) U.S. Cl.
CPC ....... *B01J 23/8872* (2013.01); *B01J 23/8876* (2013.01); *B01J 29/0308* (2013.01); *B01J 29/0341* (2013.01); *B01J 35/002* (2013.01); *B01J 35/1014* (2013.01); *B01J 35/1019* (2013.01); *B01J 35/1023* (2013.01); *B01J 35/1038* (2013.01); *B01J 35/1042* (2013.01); *B01J 35/1061* (2013.01); *B01J 37/0201* (2013.01); *C07C 5/48* (2013.01); *B01J 2523/00* (2013.01); *C07C 2523/887* (2013.01); *Y02P 20/582* (2015.11)

(56) References Cited

U.S. PATENT DOCUMENTS

| | | | |
|---|---|---|---|
| 6,921,831 | B2 | 7/2005 | Kourtakis et al. |
| 8,003,840 | B2 | 8/2011 | Oh et al. |
| 8,367,885 | B2 | 2/2013 | Chung et al. |
| 2008/0107583 | A1* | 5/2008 | Teshigahara .......... C07C 51/252 423/263 |
| 2012/0078026 | A1* | 3/2012 | Midorikawa .......... B01J 23/002 585/602 |
| 2012/0130137 | A1* | 5/2012 | Orita ...................... B01J 23/002 585/621 |

FOREIGN PATENT DOCUMENTS

| | | |
|---|---|---|
| JP | 2011148720 A | 8/2011 |
| JP | 2013-43125 A | 3/2013 |
| KR | 1998-039168 A | 8/1998 |
| KR | 10-2012-0006430 A | 1/2012 |

* cited by examiner

MESOPOROUS COMPOSITE OXIDE CATALYST, METHOD FOR PREPARING THE SAME AND METHOD FOR SYNTHESIZING 1,3-BUTADIENE USING THE SAME

This application is a National Stage Entry of International Application No. PCT/KR2014/003950, filed on May 2, 2014, which claims priority to and the benefit of Korean Patent Application Nos. 10-2013-0050408, filed on May 6, 2013 and 10-2014-0052496, filed on Apr. 30, 2014, both of which are incorporated herein by reference in their entirety.

TECHNICAL FIELD

The present invention relates to a mesoporous composite oxide catalyst, a method for preparing the same and a method for synthesizing 1,3-butadiene using the same. More particular, the present invention relates to a mesoporous composite oxide catalyst wherein a composite oxide catalyst with a large surface area is obtained by introducing certain porous silica into a multi-component bismuth-molybdate catalyst, to improve a conversion ratio of butene, and selectivity and yield of 1,3-butadiene, and provide economic efficiency, a method for preparing the same and a method for synthesizing 1,3-butadiene using the same.

BACKGROUND ART 1,3-butadiene is a representative raw material of synthetic rubbers and is one of major basic oils, the price of which sharply changes according to supply and demand situation in petrochemistry. Naphtha cracking, direct dehydrogenation of normal-butene, oxidative dehydrogenation of normal-butene and the like are used for preparation of 1,3-butadiene. Naphtha cracking for preparing 1,3-butadiene has an advantage of high price competitiveness as compared to other methods, but disadvantageously has difficulty in increasing production of only butadiene and requires large-scale investment for this purpose, because naphtha cracking is not a process for preparing only butadiene and thus relates to demand for ethylene and propylene. Advantageously, oxidative dehydrogenation of normal-butene is performed at a low temperature and reduces energy consumption because it is an exothermic reaction, unlike direct dehydrogenation, and inhibits production of carbon precipitates which poisons catalysts and thereby reduces lifespan of the catalysts, or removes the produced carbon precipitates due to addition of an oxidizing agent. Various types of metal oxides as the catalysts are used for oxidative dehydrogenation of normal-butene. In particular, bismuth-molybdate-based catalysts are known to exhibit superior catalyst activity. To increase pure bismuth-molybdate catalysts composed of only bismuth molybdenum oxide and activity thereof, multi-component bismuth-molybdate catalysts to which various metal components are added are actively researched. For example, U.S. Pat. No. 6,921,831 discloses various examples of $Q_d[Bi_aP_bMo_cO_y]_eO_x$ (Q=Cu, Au, V or a mixture thereof) catalysts, U.S. Pat. No. 8,003,840 which discloses a bismuth-molybdate catalyst containing an a phase and an γ phase which are mixed each other, and U.S. Pat. No. 8,367,885 discloses a Mo—Bi—Fe—Ni multi-component catalyst using these catalysts which has an n-butene conversion ratio of about 55 to about 65% and 1,3-butadiene yield of about 60% or less.

Co-precipitation is generally used in the preparation of the multi-component metal oxide catalyst such as bismuth-molybdate catalyst. The co-precipitation is a method of preparing catalysts by mixing two or more metal solutions under control of pH and inducing precipitation, which enables production of a powder with a high purity at a low cost due to simple process and is industrially inconvenient. However, pH and concentrations are changed as co-precipitation proceeds, thus making it difficult to obtain a powder having uniform and fine particles. In addition, a high baking temperature is required to form a crystal phase of the composite oxide catalyst, thus disadvantageously reducing the surface area of catalyst acting according to the mechanism of adsorption-reaction-desorption. Composite oxide catalysts formed of only metal oxide prepared by co-precipitation are known to generally have a surface area of 10 $m^2/g$.

EP Patent No. 2,343,123 discloses multi-component bismuth-molybdate containing at least cobalt or nickel, in which particles of silica such as fumed silica are dispersed, in order to improve surface area.

However, there is a demand for continued research associated with composite oxide catalysts with a high surface area which improves conversion ratio of butene, as well as selectivity and yield of 1,3-butadiene and enhances economic efficiency.

DISCLOSURE

Technical Problem

Therefore, the present invention has been made in view of the above problems, and the present invention obtains a high surface area by introduction of certain porous silica, thereby improving conversion ratio of butene, selectivity and yield of 1,3-butadiene and economic efficiency upon oxidative dehydrogenation of normal-butene.

That is, it is one object of the present invention to provide a novel mesoporous composite oxide catalyst which has a high surface area, as a composite oxide catalyst for synthesizing 1,3-butadiene, by addition of silica having a certain porous structure and a method for preparing the same.

It is another object of the present invention to provide a method for efficiently synthesizing 1,3-butadiene using the catalyst to improve conversion ratio of butene, and selectivity and yield of 1,3-butadiene upon oxidative dehydrogenation of normal-butene.

Technical Solution

In accordance with one aspect of the present invention, provided is a mesoporous composite oxide catalyst represented by the following Formula 1:

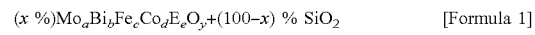

$$(x\%)Mo_aBi_bFe_cCo_dE_eO_y+(100-x)\% \ SiO_2 \qquad \text{[Formula 1]}$$

wherein E is at least one selected from Group I elements on the periodic table, a is 0.001 to 13, b, c, d and e are each independently 0.001 to 10, x is an integer of 1 to 99, and y is a value determined by other components for adjusting a valance, wherein the mesoporous composite oxide catalyst has pores, an average pore volume of the pores is 0.01 to 2 $cm^3/g$ and an average pore size of the pores is 2 to 50 nm.

In accordance with another aspect of the present invention, provided is a method for preparing a mesoporous composite oxide catalyst, the method including:

preparing a precursor mixture solution of Bi, Fe, Co and E in the following Formula 1 and a precursor solution of Mo;

adding the precursor mixture solution to the Mo precursor solution, performing co-precipitation, mixing 99 to 1% by weight of a silica powder having an average pore volume, of 0.5 to 2 cm³/g, an average pore size of 2 to 10 nm and a surface area of 500 to 1,400 m²/g with 1 to 99% by weight of the co-precipitated solution, and drying the resulting mixture, to obtain a solid powder; and molding and baking the solid powder to obtain a mesoporous composite oxide catalyst represented by the following Formula 1, including pores and having an average pore volume of 0.01 to 2 cm³/g and an average pore size of 2 to 50 nm.

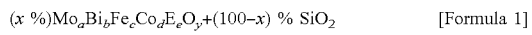

$(x\%)Mo_aBi_bFe_cCo_dE_eO_y+(100-x)\% SiO_2$  [Formula 1]

wherein E is at least one selected from Group I elements on the periodic table, a is 0.001 to 13, b, c, d and e are each independently 0.001 to 10, x is an integer of 1 to 99, and y is a value determined by other components for adjusting a valance.

In accordance with another aspect of the present invention, provided is a method for preparing a mesoporous composite oxide catalyst, the method including:

preparing a precursor mixture solution of Bi, Fe, Co and E in the following Formula 1 and a precursor solution of Mo;

adding the precursor mixture solution to the Mo precursor solution, followed by co-precipitating, drying and grinding;

mixing 1 to 99% by weight of the co-precipitated and ground product with 99 to 1% by weight of a silica powder having an average pore volume of 0.5 to 2 cm³/g, an average pore size of 2 to 10 nm and a surface area of 500 to 1,400 m²/g to obtain a solid powder; and drying and baking the solid powder to obtain a mesoporous composite oxide catalyst represented by the following Formula 1, including pores and having an average pore volume of 0.01 to 2 cm³/g and an average pore size of 2 to 50 nm.

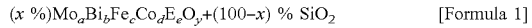

$(x\%)Mo_aBi_bFe_cCo_dE_eO_y+(100-x)\% SiO_2$  [Formula 1]

wherein E is at least one selected from Group I elements on the periodic table, a is 0.001 to 13, b, c, d and e are each independently 0.001 to 10, x is an integer of 1 to 99, and y is a value determined by other components for adjusting a valance.

Furthermore, in accordance with another aspect of the present invention, provided is a method for synthesizing 1,3-butadiene by oxidative dehydrogenation of normal-butene using the mesoporous composite metal oxide catalyst as a catalyst.

Advantageous Effects

As apparent from the fore-going, the present invention advantageously provides a composite oxide catalyst with a large surface area for synthesizing 1,3-butadiene by introducing certain porous silica into a multi-component bismuth-molybdate catalyst, thereby improving a conversion ratio of butene, and selectivity and yield of 1,3-butadiene, and having economic efficiency from the viewpoint of decreasing an amount of used metal than conventional methods and thereby reducing catalyst production cost.

BEST MODE

Hereinafter, the present invention will be described in detail.

The present invention provides a mesoporous composite oxide catalyst as a catalyst for synthesizing 1,3-butadiene.

As used herein, the term "mesoporous composite oxide catalyst" refers to a structure in which a composite oxide catalyst is sufficiently introduced into support pores as well as on the surface of a silica support, unless otherwise mentioned.

Specifically, the catalyst is represented by the following Formula 1:

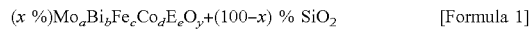

$(x\%)Mo_aBi_bFe_cCo_dE_eO_y+(100-x)\% SiO_2$  [Formula 1]

wherein E is at least one selected from Group I elements on the periodic table, a is 0.001 to 13, b, c, d and e are each independently 0.001 to 10, x is an integer of 1 to 99, and y is a value determined by other components for adjusting a valance, wherein the mesoporous composite oxide catalyst has pores, an average pore volume of the pores is 0.01 to 2 cm³/g and an average pore size of the pores is 2 to 50 nm.

In addition, the catalyst has a high surface area of 20 to 1,400 m²/g.

In a specific example, the average pore volume of the pores in the catalyst is 0.01 to 1.5 cm³/g, the average pore size is 2 to 10 nm, and the catalyst has a high surface area of 50 to 900 m²/g.

In another example, the average pore volume of the pores in the catalyst is 0.03 to 1 cm³/g, the average pore size is 2 to 5 nm, and the catalyst has a high surface area of 83 to 879 m²/g.

In Formula 1, E comprises at least one of cesium (Cs) and rubidium (Rb).

In Formula 1, a is 1 to 12 or 8 to 12.

In Formula 1, b, c, d and e are each independently 1 to 10 or 1 to 9.

In Formula 1, x is an integer of 1 to 90, or is an integer of 30 to 60.

For example, SiO₂ has an average pore volume of 0.5 to 2 cm³/g or 1.1 to 1.4 cm³/g, an average pore size of 2 to 10 nm or 3 to 5 nm, and a surface area of 500 to 1,400 m²/g or 880 to 1,337 m²/g.

Figure 5:
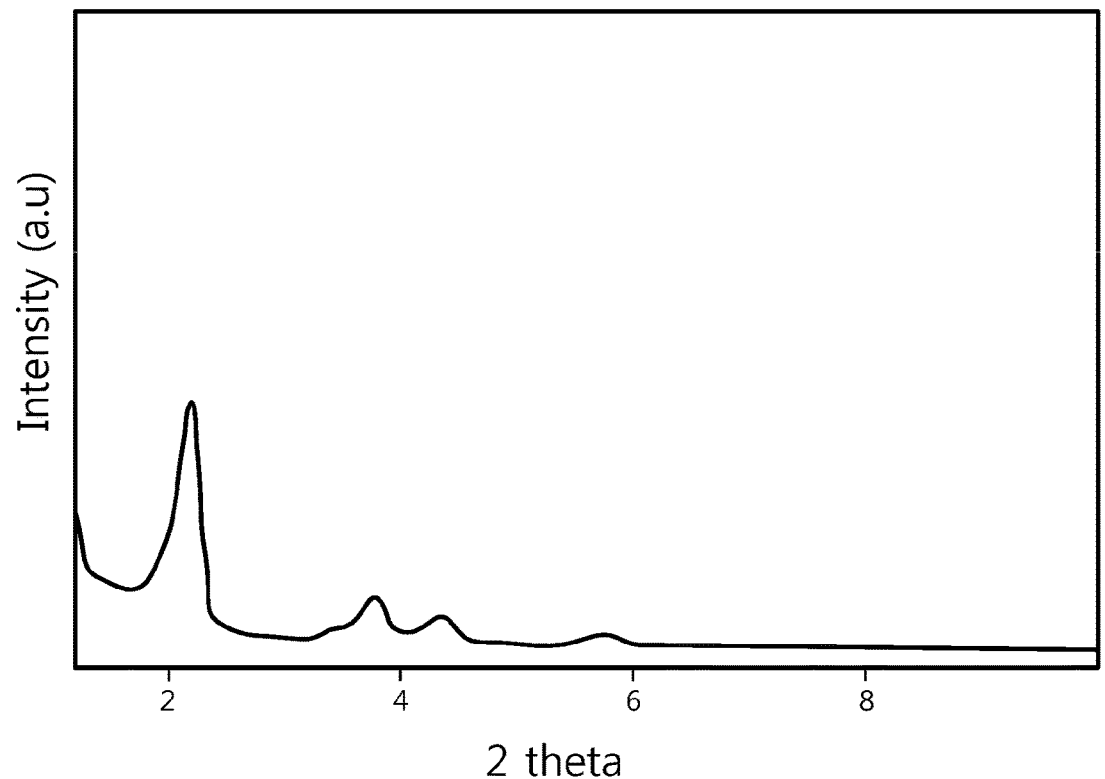
FIG. 5 is a small angle XRD spectrum of silica having an MCM-41 type of crystal structure prepared according to the flowchart shown in FIG. 1.

In a specific example, SiO₂ has an MCM-41 type of crystal structure and exhibits the spectrum of FIG. 5. For reference, the silica having an MCM-41 type of crystal structure has peaks in the 2-theta range of 1.50 to 2.38, 3.40 to 3.89, and 4.12 to 4.51 upon small angle XRD (FIG. 5).

Figure 6:
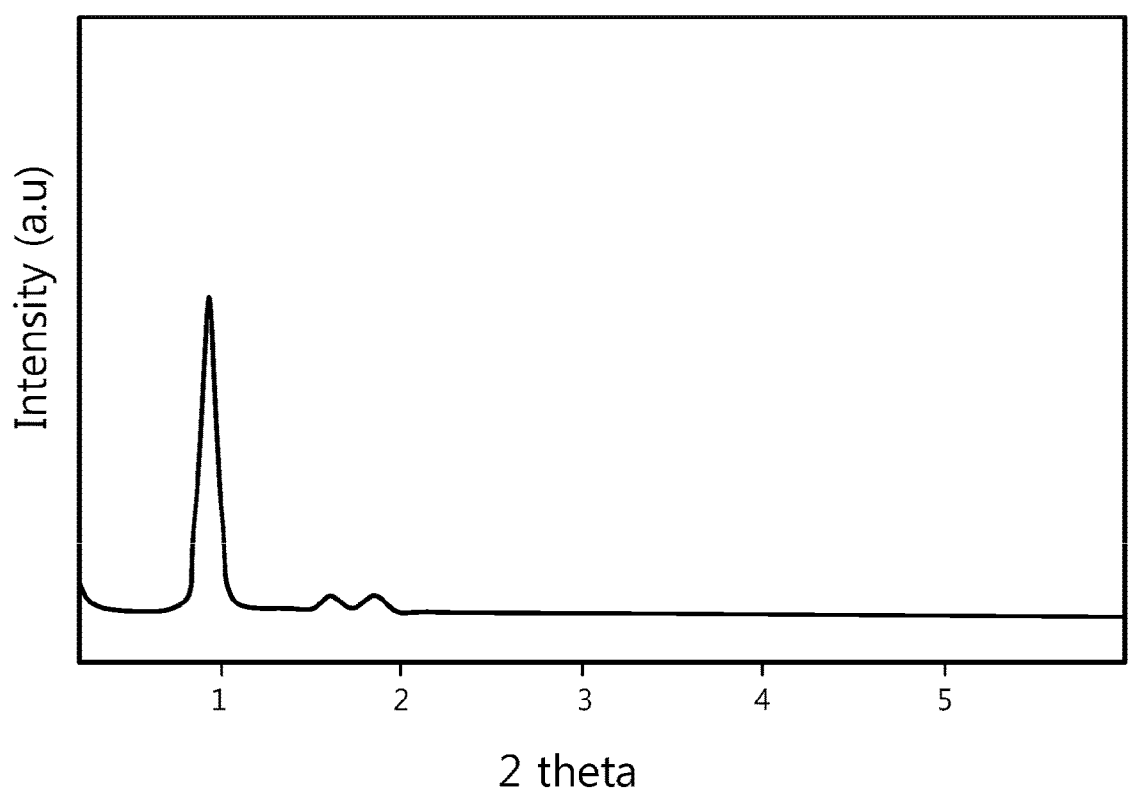
FIG. 6 is a small angle XRD spectrum of silica having an SBA-15 type of crystal structure prepared according to the flowchart shown in FIG. 2.

In another example, $SiO_2$ has an SBA-15 type of crystal structure and exhibits the spectrum of FIG. 6. For reference, the silica having an SBA-15 type of crystal structure has peaks in the 2-theta range of 0.60 to 1.18, 1.49 to 1.73, and 1.80 to 1.98 upon small angle XRD (FIG. 6).

The mesoporous composite metal oxide catalyst according to the present invention is for example prepared by the following method including:

preparing a precursor mixture solution of Bi, Fe, Co and E in the following Formula 1 and a precursor solution of Mo;

adding the precursor mixture solution to the Mo precursor solution, performing co-precipitation, mixing 99 to 1% by weight of a silica powder having an average pore volume of 0.5 to 2 $cm^3/g$, an average pore size of 2 to 10 nm and a surface area of 500 to 1,400 $m^2/g$ with 1 to 99% by weight of the co-precipitated solution, and drying the resulting mixture, to obtain a solid powder; and molding and baking the solid powder to obtain a mesoporous composite oxide catalyst represented by the following Formula 1, including pores and having an average pore volume of 0.01 to 2 $cm^3/g$ and an average pore size of 2 to 50 nm.

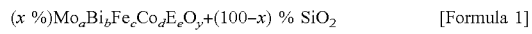

$(x\ \%)Mo_aBi_bFe_cCo_dE_eO_y+(100-x)\ \%\ SiO_2$     [Formula 1]

wherein E is at least one selected from Group I elements on the periodic table, a is 0.001 to 13, b, c, d and e are each independently 0.001 to 10, x is an integer of 1 to 99, and y is a value determined by other components for adjusting a valance.

In another embodiment, the mesoporous composite metal oxide catalyst according to the present invention is prepared by the following method including:

preparing a precursor mixture solution of Bi, Fe, Co and E in the following Formula 1 and a precursor solution of Mo;

adding the precursor mixture solution to the Mo precursor solution, followed by co-precipitating, drying and grinding;

mixing 1 to 99% by weight of the co-precipitated and ground product with 99 to 1% by weight of a silica powder having an average pore volume of the pores, of 0.5 to 2 $cm^3/g$, an average pore size of 2 to 10 nm and a surface area of 500 to 1,400 $m^2/g$; and drying and baking the solid powder to obtain a mesoporous composite oxide catalyst represented by the following Formula 1, including pores and having an average pore volume of 0.01 to 2 $cm^3/g$ and an average pore size of 2 to 50 nm.

For example, the silica powder is prepared by adding a silica source to a basic aqueous solution, in which a cationic surfactant is dispersed, or an acidic aqueous solution, in which a block copolymer is dispersed, and subjecting the resulting solution to heat or pressure treatment.

The silica obtained by drying and baking the heat- or pressure-treated solution is added to a metal precursor solution, followed by drying and baking, to obtain a mesoporous composite oxide catalyst. In addition, the average pore size of the mesoporous silica can be increased to 2 to 50 nm or more by controlling heat treatment temperature and heat treatment time or adding an expander such as trimethyl benzene (TMB).

The composite metal oxide catalyst according to the present invention is obtained by mixing metal oxide, which is prepared by co-precipitation and obtained by baking, with mesoporous silica, but the preparation method is not limited thereto.

In a specific example, the silica powder may have an MCM-41 type of crystal structure formed by stirring a cationic surfactant solution with the silica source to prepare a solution, thermally treating the solution at 333K to 373K, controlling a pH of the solution, and drying and baking the solution.

The cationic surfactant solution for example comprises at least one selected from cetyltrimethylammonium bromide, cetyltrimethylammonium chloride, decyltrimethylammonium bromide, and decyltrimethylammonium chloride.

The silica source may have a reactive group which is condensed with the surfactant and may for example comprise at least one selected from tetramethylorthosilicate, tetraethylorthosilicate and sodium silicate.

The cationic surfactant and the silica are present in a molar ratio of surfactant:silica=1:2 to 1:10. For example, the molar ratio of cationic surfactant to silica may be 1:5.

In another example, the silica powder may have a SBA type of crystal structure formed by stirring a block copolymer solution with a silica source to prepare a solution, thermally treating the solution at 333K to 373K, and drying and baking the solution.

The block copolymer may be a block copolymer containing an ethylene glycol block and a propylene glycol block and may for example comprise at least one of a diblock copolymer of an ethylene glycol block and a propylene glycol block, and a triblock copolymer containing an ethylene glycol block, a propylene glycol block and an ethylene glycol block.

The silica source may be selected from types described above.

The block copolymer and the silica are used in a molar ratio of 1:40 to 1:80. For example, the molar ratio of the block copolymer to the silica may be 1:65.

In the present invention, drying is for example carried out at 323K to 473K.

In addition, in the present invention, baking is for example carried out at 673K to 873K.

In addition, the heat- or pressure-treated silica mixture solution is dried and baked before use, but the present invention is not limited thereto.

The metal precursor solution may be a nitrate salt, an ammonium salt or the like.

For example, in Formula 1, when cesium is selected as an E component, cesium, cobalt, iron and bismuth precursors are simultaneously dissolved in distilled water, a molybdenum precursor is separately dissolved in distilled water and the precursor mixture solution is then mixed with the molybdenum precursor solution. In order to increase solubility of the respective precursors, an acidic solution (for example, nitric acid) or the like may be added. When the precursors are completely dissolved, a precursor solution containing cesium, cobalt, iron and bismuth is added to the precursor solution containing molybdenum and metal components are then co-precipitated. The co-precipitated solution is stirred for 0.5 to 24 hours, preferably, 1 to 2 hours for sufficient stirring.

The mesoporous silica is added to the stirred solution, and the resulting mixture is dried at 323K to 473K for 12 to 24 hours to remove moisture and other liquid components and thereby obtain a solid sample. The solid sample thus obtained is molded into a hollow, pellet or sphere form and thermally treated in an electric furnace at a temperature of 673K to 873K to prepare a composite oxide catalyst, but the present invention is not limited thereto. The composite oxide catalyst may be prepared by mixing the mesoporous silica with the dried sample of the stirred solution during molding, but the present invention is not limited thereto.

The catalyst may be applied to oxidative dehydrogenation of normal-butene, but the present invention is not limited thereto. Specifically, 1,3-butadiene can be synthesized by oxidative dehydrogenation of normal-butene using the catalyst described above.

According to the present invention, normal-butene as a reactant is adsorbed onto a catalyst, oxygen in the catalyst lattice is reacted with two hydrogen of butene to produce 1,3-butadiene and water, and the reaction proceeds in a way that an oxygen molecule as the reactant fills the vacant oxygen position of the catalyst lattice.

The oxidative dehydrogenation is carried out by reacting a reactant containing normal-butene, oxygen, nitrogen and steam in a molar ratio of 1:0.5 to 2:2 to 20:5 to 20 using the catalyst at a reaction temperature of 250 to 350° C. and at a space velocity of 50 to 5,000 $h^{-1}$, based on butene.

For example, the reaction temperature and the space velocity are within the range of 280 to 330° C. and 50 to 1000 $h^{-1}$, based on butene, respectively.

In addition, the oxidative dehydrogenation is carried out by charging the catalyst as a fixed bed in a shell-tube reactor including a multiple fixed tube and being provided at an outside thereof with a heat medium circulation unit and continuously passing the reactant through the catalyst layer.

For example, the oxidative dehydrogenation is carried out using a shell-tube reactor including a multiple fixed tube filled with 1,000 to 2,000 cc of the catalyst and being provided at an outside thereof with a heat medium circulation unit.

The method for synthesizing 1,3-butadiene according to the present invention may include charging the composite oxide catalyst prepared according to the preparation method as a fixed bed; performing oxidative dehydrogenation of a reactant containing a butene-containing C4 mixture, oxygen, nitrogen and steam while continuously passing the reactant through the catalyst layer of the reactor to obtain a dehydrogenation product mixture; and purification of separating 1,3-butadiene from the dehydrogenation product mixture. The method may further include recycling the reactant, if necessary.

For example, the obtained 1,3-butadiene may be subjected to purification including quenching, compression, absorbance, degassing and separation of butadiene. Specifically, water and heavy ingredients are removed from the product discharged from the reactor by quenching and the resulting product is subjected to the absorbance process through compression at a pressure appropriate for absorbance.

In the absorbance process, 1,3-butadiene is absorbed using a solvent and is separated from nitrogen, oxygen and $CO_x$. In the degassing process, gas and by-products absorbed together with the solvent are removed. Finally, 1,3-butadiene is separated from the solvent by separation of the butadiene based on the difference in physical properties. If necessary, the method may further include circulating the starting material of the respective steps.

Hereinafter, the present invention will be described in detail with reference to examples, but the examples should not be construed as limiting the scope and spirit of the present invention.

EXAMPLE 1

For preparation of porous silica, cetyltrimethylammonium bromide (CTABr) as a surfactant was dissolved in 60° C. distilled water, a sodium silicate solution was added to the solution at a stoichiometric ratio of 0.12 $Na_2O$:0.5 $SiO_2$:0.1 CTABr:30 $H_2O$, and was stirred at 60° C. for one hour to prepare an emulsion.

The emulsion was thermally treated at 100° C. for 48 hours, and pH changed as synthesis processed was titrated with an aqueous nitric acidic solution or an aqueous hydrochloric acidic solution to maintain pH 10, thereby preparing a silica mixture solution containing silica. The silica mixture solution was filtered, washed with distilled water or ethanol and dried at 100° C. to obtain a solid sample.

The solid sample was baked in an electric furnace at 550° C. for 5 hours and the prepared silica was added to the metal precursor solution using Cs as E in Formula 1 to prepare a composite oxide catalyst.

For reference, as the metal precursors, cobalt nitrate ($Co(NO_3)_2 \cdot 6H_2O$), iron nitrate ($Fe(NO_3)_3 \cdot 9H_2O$), bismuth nitrate ($Bi(NO_3)_2 \cdot 5H_2O$), cesium nitrate ($CsNO_3$) and ammonium molybdate ($(NH_4)6Mo_7O_{24} \cdot 4H_2O$) were used.

Specifically, bismuth nitrate, cesium nitrate, cobalt nitrate and iron nitrate were dissolved in an aqueous nitric acid solution and the solution was stirred to prepare an aqueous metal nitrate solution.

Separately, ammonium molybdate was dissolved in distilled water in a double jacket reactor while maintaining 40° C., the aqueous metal nitrate solution was added to the solution while stirring and the resulting mixture was stirred at 40° C. for one hour.

Figure 1:
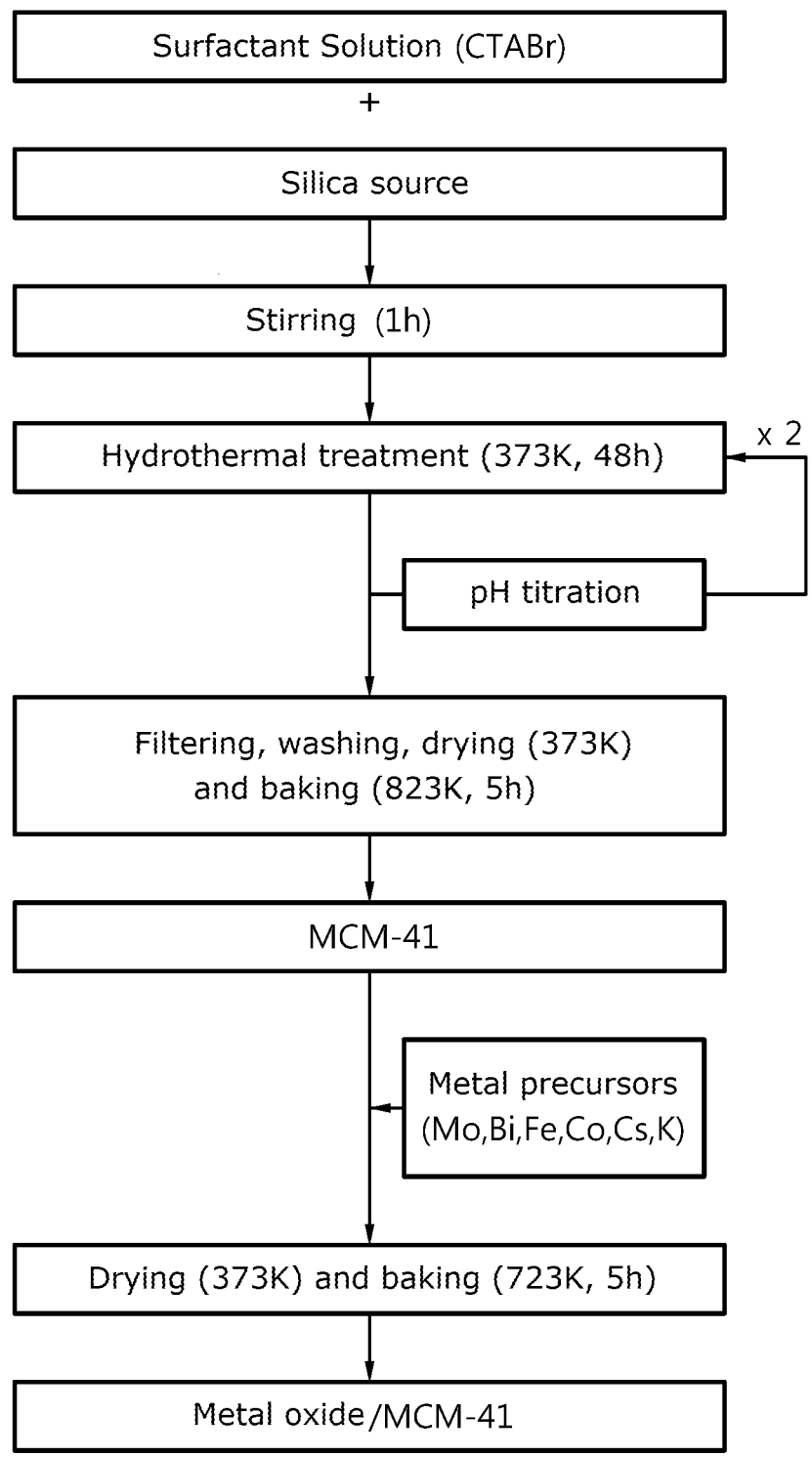
FIG. 1 is a flowchart illustrating a process of synthesizing a composite oxide catalyst containing silica having an MCM-41 type of crystal structure according to a first embodiment of the present invention.

The stirred solution was dried in a 120° C. oven for 18 hours and then ground, and the mesoporous silica was added thereto to obtain a solid powder. The solid powder was kneaded with distilled water and alcohol, extrusion-molded into a pellet having a diameter of 6 mm, and a length of 6 mm, and the molded product was thermally treated at 450° C. in an electric furnace for 7 hours to prepare a mesoporous composite metal oxide catalyst having a composition of 30 wt % $Mo_{12}Bi_1Fe_2Co_5Cs_{0.10}Oy$+70 wt % $SiO_2$ and a mesoporous composite metal oxide catalyst having a composition of 60 wt % $Mo_{12}Bi_1Fe_2Co_5Cs_{0.10}Oy$+40 wt % $SiO_2$, respectively. The preparation process of the catalyst is shown in FIG. 1.

EXAMPLE 2

For preparation of porous silica, the triblock copolymer (produced by BASF Corp.) of poly(ethylene glycol)-poly(propylene glycol)-poly(ethylene glycol) was dissolved in a 40° C. hydrochloric acid solution, and tetraethylortho silicate (TEOS) was added to the solution and was stirred for one hour to prepare an emulsion.

The emulsion was thermally treated at 40° C. for 24 hours and at 100° C. for 12 hours, to prepare a silica mixture solution. The silica mixture solution was filtered, washed with distilled water or ethanol and dried at 100° C. to obtain a solid sample.

The solid sample was baked in an electric furnace at 550° C. for 5 hours and the prepared silica was added to the metal precursor solution using Cs as E in Formula 1 to prepare a composite oxide catalyst.

For reference, as the metal precursors, cobalt nitrate ($Co(NO_3)_2 \cdot 6H_2O$), iron nitrate ($Fe(NO_3)_3 \cdot 9H_2O$), bismuth nitrate ($Bi(NO_3)_2 \cdot 5H_2O$), cesium nitrate ($CsNO_3$) and ammonium molybdate ($(NH_4)6Mo_7O_{24} \cdot 4H_2O$) were used.

Specifically, bismuth nitrate, cesium nitrate, cobalt nitrate and iron nitrate were dissolved in an aqueous nitric acid solution and the solution was stirred to prepare an aqueous metal nitrate solution.

Separately, ammonium molybdate was dissolved in distilled water in a double jacket reactor while maintaining 40° C., the aqueous metal nitrate solution was added to the solution while stirring and the resulting mixture was stirred at 40° C. for one hour.

Figure 2:
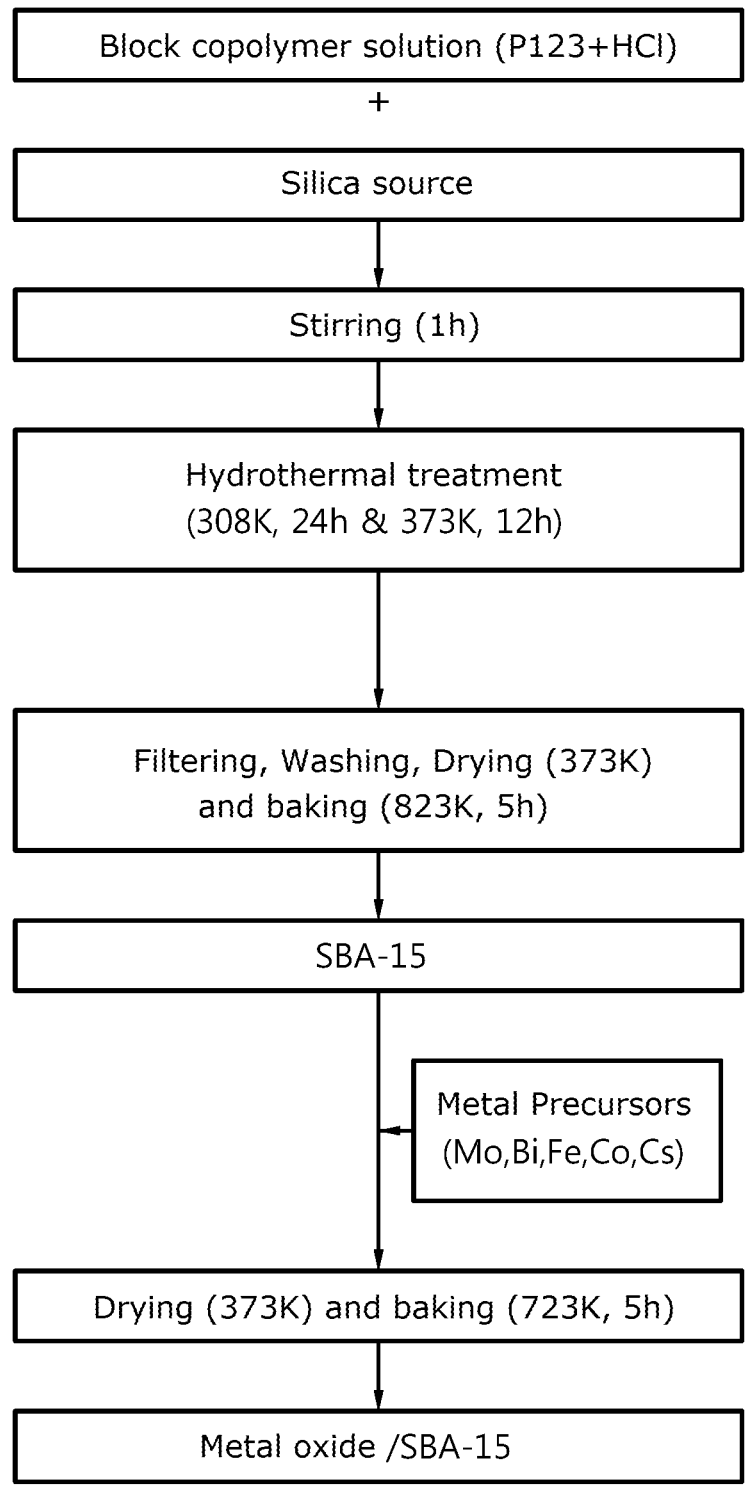
FIG. 2 is a flowchart illustrating a process of synthesizing a composite oxide catalyst containing silica having an SBA-15 type of crystal structure according to a second embodiment of the present invention.

The stirred solution was dried in a 120° C. oven for 18 hours and then ground, and the mesoporous silica was added thereto to obtain a solid powder. The solid powder was kneaded with distilled water and alcohol, extrusion-molded into a pellet having a diameter of 6 mm, and a length of 6 mm, and the molded product was thermally treated at 450° C. in an electric furnace for 7 hours to prepare a mesoporous composite metal oxide catalyst having a composition of 30 wt % $Mo_{12}Bi_1Fe_2Co_5Cs_{0.10}Oy$+70 wt % $SiO_2$ and a mesoporous composite metal oxide catalyst having a composition of 60 wt % $Mo_{12}Bi_1Fe_2Co_5Cs_{0.10}Oy$+40 wt % $SiO_2$, respectively. The preparation process of the catalyst is shown in FIG. 2.

COMPARATIVE EXAMPLE 1

A metal catalyst using Cs as E in Formula 1 was prepared using cobalt nitrate ($Co(NO_3)_2.6H_2O$), iron nitrate ($Fe(NO_3)_3.9H_2O$), bismuth nitrate ($Bi(NO_3)_2.5H_2O$), cesium nitrate ($CsNO_3$) and ammonium molybdate (($NH_4)_6Mo_7O_{24}.4H_2O$) by the following method.

Specifically, bismuth nitrate, cesium nitrate, cobalt nitrate and iron nitrate were dissolved in an aqueous nitric acid solution and the solution was stirred to prepare an aqueous metal nitrate solution.

Separately, ammonium molybdate was dissolved in distilled water in a double jacket reactor while maintaining 40° C., the aqueous metal nitrate solution was added to the solution while stirring and the resulting mixture was stirred at 40° C. for one hour.

Figure 3:
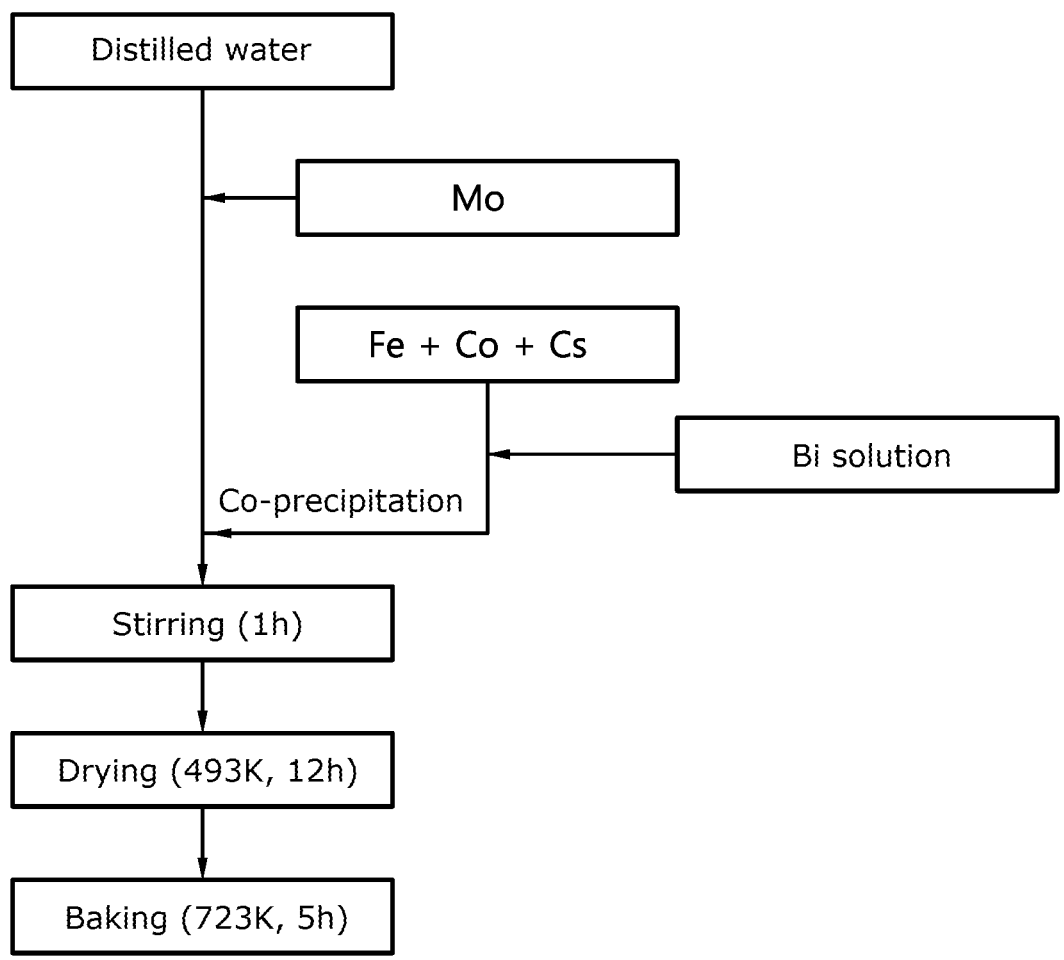
FIG. 3 is a flowchart illustrating a process of synthesizing a metal oxide catalyst by co-precipitation according to a conventional method.

The stirred solution was dried in a 120° C. oven for 18 hours and was ground, and a resulting powder was kneaded with distilled water and alcohol, extrusion-molded into a pellet having a diameter of 6 mm and a length of 6 mm, and the molded product was thermally treated at 450° C. in an electric furnace for 7 hours to prepare a mesoporous composite metal oxide catalyst having a composition of $Mo_{12}Bi_1Fe_2Co_5Cs_{0.10}Oy$. The preparation process of the catalyst is shown in FIG. 3.

X-ray diffraction and ICP-AES results showed successful preparation of the catalysts obtained in Examples 1 to 2 and Comparative Example 1. From results of X-ray diffraction analysis, it was confirmed that the catalyst was obtained as a mixed phase of $CoMoO_4$, $(Co_{0.7}Fe_{0.3})MoO_4$ and $Bi_2Mo_3O_{12}$, an element ratio of the catalyst prepared by ICP-AES was Mo:Bi:Fe:Co:Cs of 12:1:2:5:0.1 when the element ratio was calculated as a relative ratio of other metal component to Bi.

Figure 4:
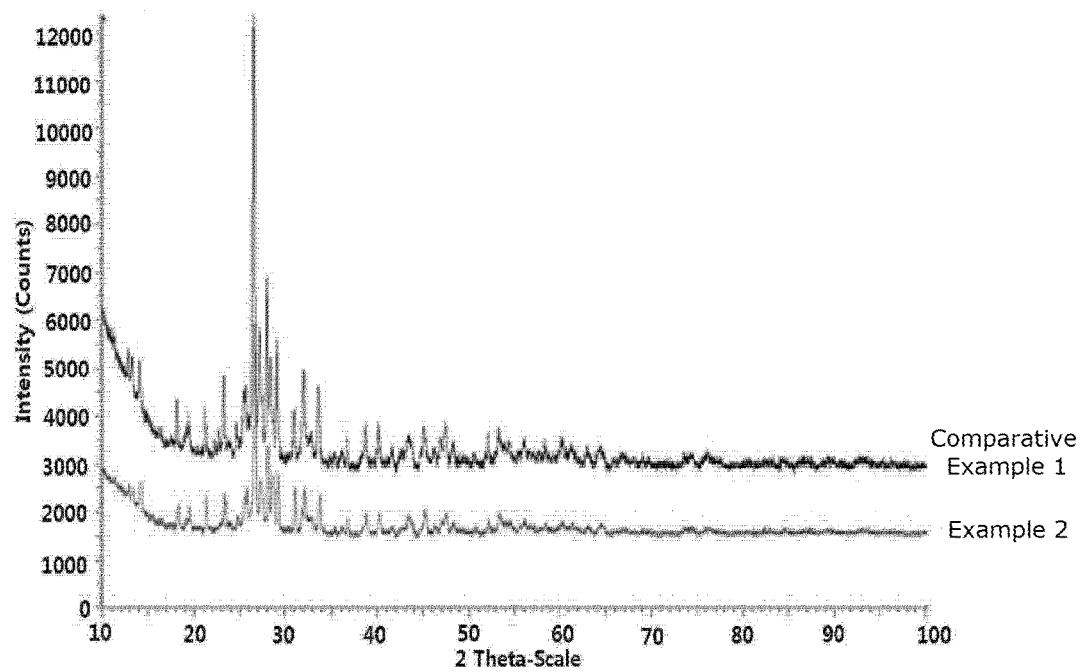
FIG. 4 is an X-ray diffraction spectrum of the metal oxide catalyst prepared according to the flowchart shown in FIG. 3 and the composite oxide catalyst prepared according to the flowchart shown in FIG. 2 and containing 40 wt % of silica having an SBA-15 type of crystal structure.

For example, X-ray diffraction spectra of the 60 wt % $Mo_{12}Bi_1Fe_2Co_5Cs_{0.10}Oy$+40 wt % $SiO_2$ catalyst corresponding to Example 2 prepared according to the present invention and the catalyst of Example 1 prepared by coprecipitation according to a conventional method are shown in FIG. 4. For reference, X-ray diffraction analysis of the mesoporous composite oxide catalyst corresponding to Example 2 showed that the mesoporous composite oxide catalyst has peaks in the 2-theta range of 9.84 to 9.96, 13.02 to 13.20, 18.62 to 18.70, 23.18 to 23.26, 25.54 to 25.62, 26.38 to 26.46, 28.30 to 28.38, 32.00 to 32.08, 33.58 to 33.66, and 45.04 to 45.12 (FIG. 4).

For reference, as shown in FIG. 4, the 2-theta peak ranges of the catalyst according to Example 2 are the same as the 2-theta ranges of 9.84 to 9.96, 13.02 to 13.20, 18.62 to 18.70, 23.18 to 23.26, 25.54 to 25.62, 26.38 to 26.46, 28.30 to 28.38, 32.00 to 32.08, 33.58 to 33.66, and 45.04 to 45.12 of the catalyst according to Comparative Example 1. This means that, in Example 2 produced according to the present invention, the same catalyst crystal phase as in Comparative Example 1 was successfully produced.

As a result of small angle XRD analysis of the mesoporous silica prepared for addition to the catalyst in Example 1 (the 2-theta value at an X axis in the spectrum is 5 degrees or less; small angle XRD), a crystal structure of MCM-41, which was a type of mesoporous silica prepared under the basic atmosphere using CTABr as a surfactant, was observed. This spectrum is shown in FIG. 5.

For reference, MCM-41 has a structure in which cylindrical mesopores having a size of 2 to 50 nm satisfying the range defined according to IUPAC are three-dimensionally well arrayed and the spectrum of FIG. 5 corresponds to characteristic peaks thereof. The silica having an MCM-41 type of crystal structure prepared according to the flowchart shown in FIG. 1 exhibits peaks in the 2-theta range of 1.50 to 2.38, 3.40 to 3.89, and 4.12 to 4.51 upon small angle XRD (FIG. 5).

In addition, the surface area, the average pore volume and the average pore size of the MCM-41 type porous silica were calculated by BET, t-plot and BJH, respectively, based on adsorption isotherm of nitrogen. As a result, the porous silica had a surface area of 1,337 $m^2$/g, an average pore volume of 1.4 $cm^3$/g and an average pore size of 3.0 nm.

The mesoporous composite metal oxide catalyst having a composition of 30 wt % $Mo_{12}Bi_1Fe_2Co_5Cs_{0.10}Oy$+70 wt % $SiO_2$ prepared by adding the porous silica having the characteristics in Example 1, and a mesoporous composite metal oxide catalyst having a composition of 60 wt % $Mo_{12}Bi_1Fe_2Co_5Cs_{0.10}Oy$+40 wt % $SiO_2$ had the surface area, the average pore volume and the average pore size as shown in the following Table 1.

TABLE 1

| Catalyst | Surface area [$m^2$/g] | Average pore volume [$cm^3$/g] | Average pore size [nm] |
|---|---|---|---|
| 30 wt % MoBiFeCoCs + 70 wt % MCM-41 | 870 | 1.0 | 2.9 |
| 60 wt % MoBiFeCoCs + 40 wt % MCM-41 | 83 | 0.3 | 2.0 |

As a result of small angle XRD of the silica prepared for addition to the catalyst in Example 2, a crystal structure of an SBA-15 type which was mesoporous silica prepared under the acidic atmosphere using a block copolymer was observed. This spectrum is shown in FIG. 6.

For reference, SBA-15 has a structure in which cylindrical mesopores having a size of 2 to 50 nm satisfying the range defined according to IUPAC are three-dimensionally well arrayed and the pores are connected to one another and the spectrum of FIG. 6 corresponds to characteristic peaks thereof. The silica having an SBA-15 type of crystal structure prepared according to the flowchart shown in FIG. 2 exhibits peaks in the 2-theta range of 0.60 to 1.18, 1.49 to 1.73, and 1.80 to 1.98 upon small angle XRD (FIG. 6).

Also, the porous silica had a surface area of 880 $m^2$/g, an average pore volume of 1.1 $cm^3$/g and an average pore size of 5.0 nm.

The mesoporous composite metal oxide catalyst having a composition of 30 wt % $Mo_{12}Bi_1Fe_2Co_5Cs_{0.10}Oy$+70 wt %

SiO$_2$ prepared by adding the porous silica having the characteristics in Example 2, and a mesoporous composite metal oxide catalyst having a composition of 60 wt % Mo$_{12}$Bi$_1$Fe$_2$Co$_5$Cs$_{0.10}$O$_y$+40 wt % SiO$_2$ had the surface area, the average pore volume and the average pore size as shown in the following Table 2.

TABLE 2

| Catalyst | Surface area [m$^2$/g] | Average pore volume [cm$^3$/g] | Average pore size [nm] |
|---|---|---|---|
| 30 wt % MoBiFeCoCs + 70 wt % SBA-15 | 619 | 1.0 | 5.0 |
| 60 wt % MoBiFeCoCs + 40 wt % SBA-15 | 141 | 0.5 | 4.3 |

Meanwhile, physical properties of the metal oxide catalyst prepared according to a conventional method in Comparative Example 1 by nitrogen adsorption like as in Examples 1 to 2 were measured. As a result, it was found that the surface area was 3.3 m$^2$/g, the average pore volume was 0.01 cm$^3$/g, and the average pore size was 39 nm.

APPLICATION EXAMPLE 75 mL of the 60 wt % MoBiFeCoCs+40 wt % SiO$_2$ mesoporous composite metal oxide catalyst obtained in Examples 1 and 2 and 75 mL of the composite metal oxide catalyst obtained in Comparative Example 1 were charged in a metal tubular reactor as a fixed bed and catalyst activity of the catalysts were measured.

Normal-butene was fed into the reactor together with oxygen, nitrogen and steam, a molar ratio of butene to oxygen to nitrogen to steam was set at 1:0.5:8:5 and space velocity (GHSV) was 250 h$^{-1}$ based on normal-butene.

A butene flow was controlled using a mass flow controller (MFC) for liquid, oxygen and nitrogen was fed using a mass flow controller for gas, and steam was injected using a liquid pump. The steam was injected as water using a vaporizer, vaporized at 200° C. and was injected into the reactor as a mixture with other reactants, butene, oxygen and nitrogen.

The catalyst was pre-treated at 400° C. for 2 hours under an air atmosphere before injection of the reactant, the reactants were continuously injected into the catalyst layer while maintaining the reaction temperature at 320° C., and reaction proceeded. Then, the resulting product was analyzed by gas chromatography at an interval of 1 to 2 hours.

The product flow contained, in addition to the target, 1,3-butadiene, carbon dioxide, carbon monooxide, C4 by-products, normal-butene, trans-2-butene, cis-2-butene, oxygen, nitrogen and the like.

Normal-conversion ratio of butene (X), selectivity (S_BD) of 1,3-butadiene and yield (Y) were calculated. Obtained results are shown in the following Table 3 and conversion ratio (X), selectivity (S_BD) and yield (Y) in Table 3 are calculated by the following Equations 1, 2 and 3.

Conversion ratio (%)=the number of moles of reacted normal-butene/the number of moles of supplied normal-butene×100    [Equation 1]

Selectivity (%)=the number of moles of produced 1,3-butadiene/the number of moles of reacted normal-butene×100    [Equation 2]

Yield (%)=the number of moles of produced 1,3-butadiene/the number of moles of supplied normal-butene×100    [Equation 3]

TABLE 3

| Types | X (%) | S_BD (%) | Y (%) | Hot spot (° C.) |
|---|---|---|---|---|
| Example 1 | 75.1 | 94.7 | 71.1 | 369 |
| Example 2 | 83.9 | 95.9 | 80.5 | 372 |
| Comparative Example 1 | 70.3 | 92.1 | 64.7 | 362 |

As can be seen from Table 3 above, Examples 1 to 2 containing the porous silica according to the present invention exhibited improved conversion ratio of normal-butene, selectivity of 1,3-butadiene and yield, as compared to Comparative Example 1, the metal oxide catalyst containing no porous silica prepared by a conventional method.

Furthermore, in Examples 1 to 2 according to the present invention, certain porous silica is substituted for a predetermined content or more, for example, 40 wt % or more, of the composite oxide catalyst for synthesizing 1,3-butadiene, and the amount of used metal was thus less than in the case of a conventional catalyst, thus providing economic efficiency capable of reducing preparation cost.

Consequently, it can be seen that the mesoporous composite metal oxide catalyst for synthesizing 1,3-butadiene having larger surface area and improved catalyst performance and economic efficiency than in the case of a conventional method can be obtained by introducing certain porous silica into preparation of catalyst for synthesizing 1,3-butadiene.

What is claimed is:

1. A method for synthesizing 1,3-butadiene, comprising: oxidatively dehydrogenating normal-butene in the presence of a mesoporous composite metal oxide catalyst to produce 1,3-butadiene,
wherein:
the mesoporous composite metal oxide catalyst is represented by the following Formula 1:

(x %)Mo$_a$Bi$_b$Fe$_c$Co$_d$E$_e$O$_y$+(100−x)% SiO$_2$    [Formula 1]

wherein E is at least one element selected from Group I elements on the periodic table, a is 0.001 to 13, b, c, d and e are each independently 0.001 to 10, x is an integer of 30 to 60, and y is a value determined by other components for adjusting a valance;
the mesoporous composite metal oxide catalyst has a surface area of 50 to 900 m$^2$/g and;
the mesoporous composite metal oxide catalyst has pores, an average pore volume of the pores is 0.01 to 2 cm$^3$/g and an average pore size is 2 to 50 nm.

2. The method according to claim 1, wherein the oxidative dehydrogenation is carried out by reacting a reactant containing normal-butene, oxygen, nitrogen and steam at molar ratios of 1:0.5 to 2:2 to 20:5 to 20 in the presence of the mesoporous composite metal oxide catalyst at a reaction temperature of 250 to 350° C. and at a space velocity of 50 to 5,000 h$^{-1}$.

3. The method of claim 1, wherein the mesoporous composite metal oxide catalyst is charged as a fixed bed in a metal tubular reactor or a shell-tube reactor containing multiple fixed tubes.

4. The method of claim 1, further comprising pretreating the catalyst at 400° C. for 2 hours under an air atmosphere.

5. The method of claim 3, wherein the catalyst is present in the reactor as a layer and the reactants are continuously injected into the catalyst layer while maintaining a reaction temperature at 320° C.

6. The method of claim 1, wherein the oxidative dehydrogenation is carried out at a space velocity of from 50 to 250 $h^{-1}$.

7. The method of claim 1, wherein the $SiO_2$ is a porous silica having an average pore size of 2 to 10 nm and a surface area of 500 to 1,400 $m^2/g$.

8. The method of claim 1, wherein the $SiO_2$ has an MCM-41 type of crystal structure.

9. The method of claim 1, wherein the $SiO_2$ has a SBA-15 type of crystal structure.

10. The method of claim 1, wherein the mesoporous composite metal oxide catalyst has an average pore volume of 0.01 to 1.5 $cm^3/g$ and an average pore size of 2 to 10 nm.

11. The method of claim 1, wherein the mesoporous composite metal oxide catalyst has an average pore volume of 0.03 to 1 $cm^3/g$, an average pore size of 2 to 5 nm, and a surface area of 83 to 879 $m^2/g$.

12. The method of claim 1, further comprising a purification process comprising absorbing the 1,3-butadiene using a solvent to separate 1,3-butadiene from nitrogen and oxygen.

13. The method of claim 12, further comprising a degassing process to remove gas and by-products from the solvent.

14. The method of claim 12, further comprising a separation process to separate the 1,3-butadiene from the solvent.

* * * * *